United States Patent
Dominguez et al.

(10) Patent No.: US 6,572,628 B2
(45) Date of Patent: Jun. 3, 2003

(54) METHOD AND APPARATUS FOR PLACING A MEDICAL AGENT INTO A VESSEL OF THE BODY

(75) Inventors: Larry Dominguez, West Miami, FL (US); Ajay K. Wakhloo, Key Biscayne, FL (US)

(73) Assignee: Cordis Neurovascular, Inc., Miami Lakes, FL (US)

( * ) Notice: Subject to any disclaimer, the term of this patent is extended or adjusted under 35 U.S.C. 154(b) by 150 days.

(21) Appl. No.: 09/894,735

(22) Filed: Jun. 28, 2001

(65) Prior Publication Data

US 2003/0004532 A1 Jan. 2, 2003

(51) Int. Cl.[7] .............................................. A61B 17/08
(52) U.S. Cl. ....................................... 606/151; 606/108
(58) Field of Search ............................. 606/108, 151, 606/194, 159, 213, 191, 198, 1, 200; 604/93.01, 264, 96.01, 104–109; 600/106, 107

(56) References Cited

U.S. PATENT DOCUMENTS

| | | | |
|---|---|---|---|
| 2,688,329 A | 9/1954 | Wallace | |
| 4,790,331 A | 12/1988 | Okada et al. | |
| 5,108,407 A | 4/1992 | Geremia et al. | |
| 5,122,136 A | 6/1992 | Guglielmi et al. | |
| 5,263,964 A | 11/1993 | Purdy | |
| 5,325,860 A | * 7/1994 | Seward et al. | 600/468 |
| 5,334,210 A | 8/1994 | Gianturco | |
| 5,345,940 A | * 9/1994 | Seward et al. | 600/463 |
| 5,350,397 A | 9/1994 | Palermo et al. | |
| 5,382,259 A | 1/1995 | Phelps et al. | |
| 5,443,454 A | * 8/1995 | Tanabe et al. | 604/264 |
| 5,464,395 A | 11/1995 | Faxon et al. | |
| 5,667,493 A | 9/1997 | Janacek | |
| 5,776,114 A | 7/1998 | Frantzen et al. | |
| 5,779,669 A | 7/1998 | Haissaguerre et al. | |
| 5,836,957 A | 11/1998 | Schulz et al. | |
| 5,846,223 A | 12/1998 | Swartz et al. | |
| 5,853,418 A | 12/1998 | Ken et al. | |
| 5,873,842 A | 2/1999 | Brennen et al. | |
| 5,885,238 A | 3/1999 | Stevens et al. | |
| 5,911,725 A | 6/1999 | Boury | |
| 5,916,194 A | 6/1999 | Jacobsen et al. | |
| 6,024,754 A | * 2/2000 | Engelson | 606/213 |
| 6,113,622 A | 9/2000 | Hieshima | |
| 6,126,649 A | 10/2000 | Van Tassel et al. | |
| 6,179,857 B1 | 1/2001 | Diaz et al. | |
| 6,183,491 B1 | 2/2001 | Lulo | |

* cited by examiner

*Primary Examiner*—Gloria M. Hale
*Assistant Examiner*—Tejash D Patel
(74) *Attorney, Agent, or Firm*—Henry W. Collins

(57) ABSTRACT

A method and apparatus for placing a medical agent, such as an embolic coil into a vessel, or aneurysm, by utilizing a stabilizing catheter to retain or support a medical agent deployment device.

8 Claims, 3 Drawing Sheets

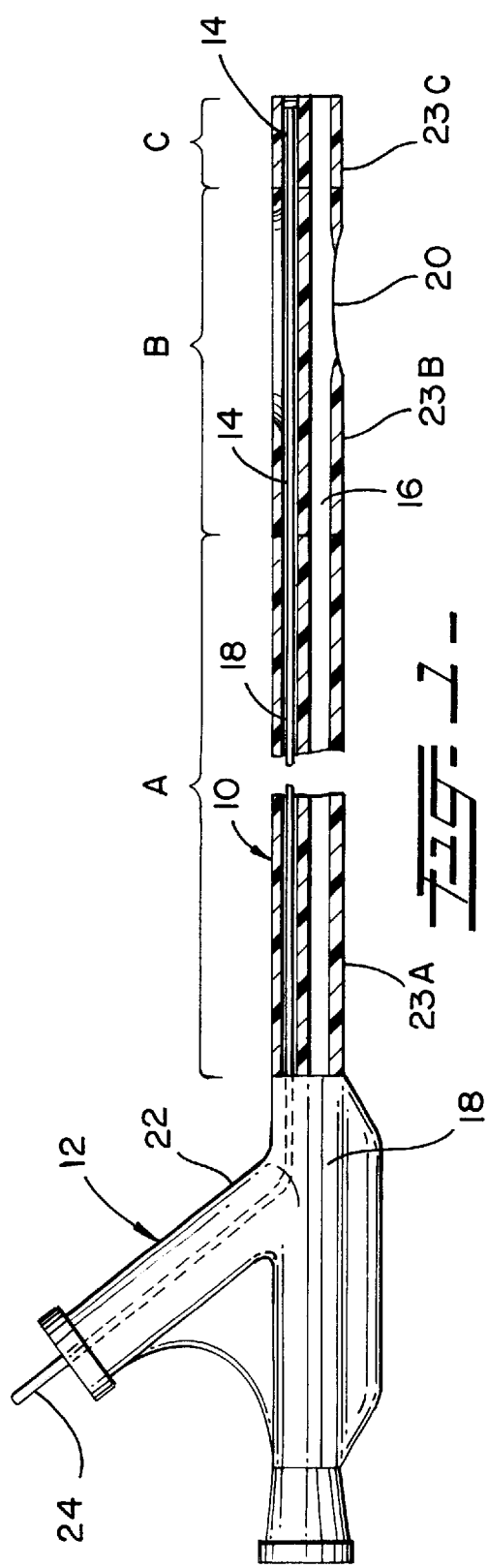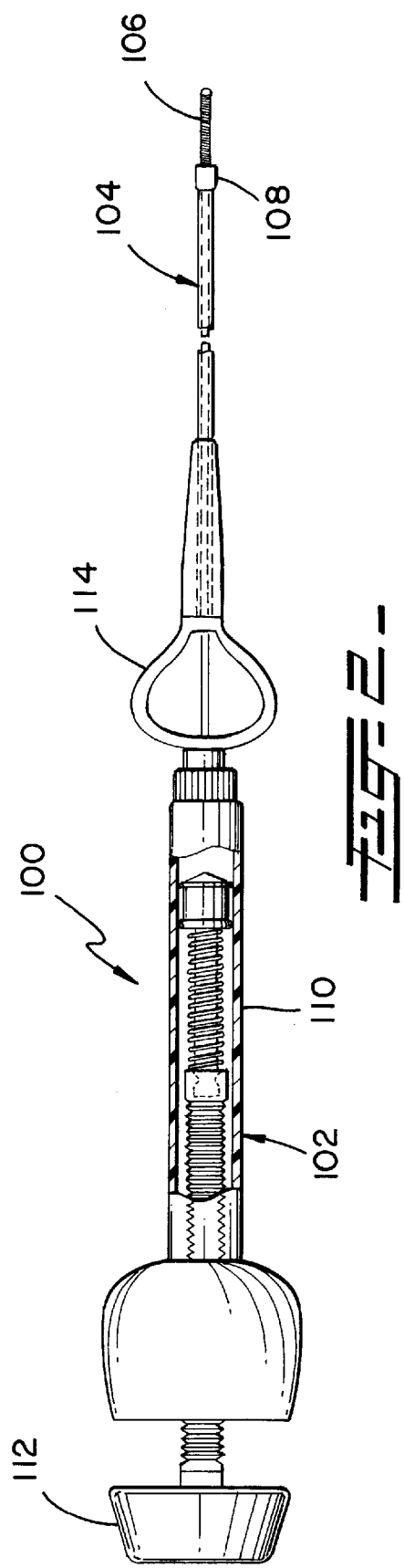

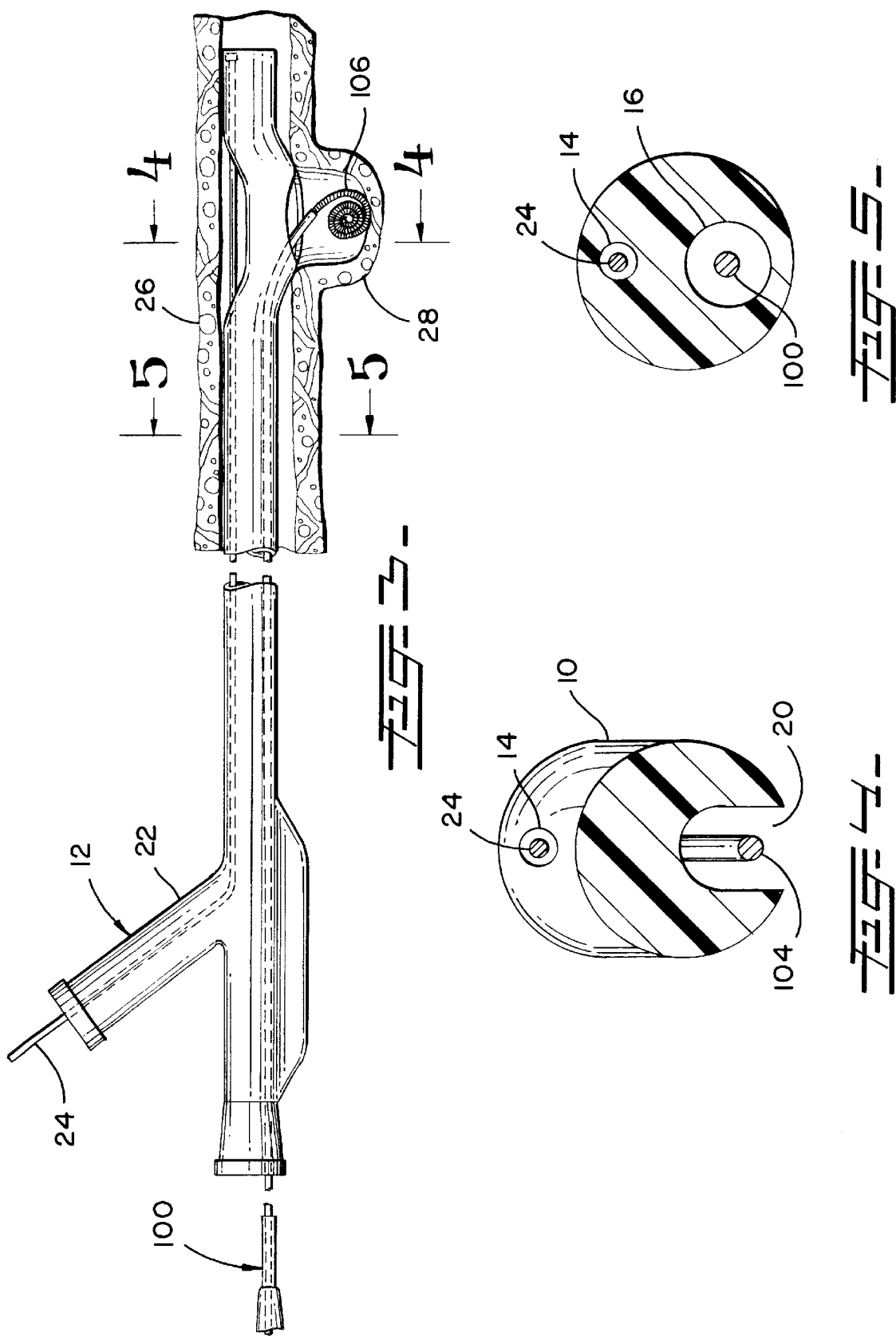

METHOD AND APPARATUS FOR PLACING A MEDICAL AGENT INTO A VESSEL OF THE BODY

BACKGROUND OF THE INVENTION

1. Field of the Invention

This invention concerns a novel method and apparatus for placing a medical agent into a vessel of the body, and in particular concerns a novel method for placing embolic coils within an aneurysm of the brain.

2. Description of the Prior Art

The use of embolic coils placed within an aneurysm for treating the aneurysm within the brain is well known. Various devices are known for delivering embolic coils through the patient's vessel to the aneurysm. Typically these embolic coils, which generally take the form of helically wound coils, or random wound coils, are carried by a coil deployment device which serves to introduce the coils into the aneurysm. The coils are then released by the coil deployment device using one of various types of release mechanisms.

An example of such a coil deployment device is disclosed in U.S. Pat. No. 6,113,622 entitled, "Embolic Coil Hydraulic Deployment System", issued Sep. 5, 2000 and assigned to the same assignee as the present patent application. The disclosure of this patent is incorporated herein and made a part of this application. It has been found to be difficult to place these coils in the exact desired position because of the relative lack of stability of the deployment device within the vessel during the introduction of the embolic coil to an aneurysm. An example of a delivery system used to stabilize a coil deployment device is disclosed in U.S. patent application Ser. No. 09/878,530, entitled "Delivery System Using Balloon Catheter", filed Jun. 11, 2001 and assigned to the same assignee as the present patent application. The disclosure in this patent application is incorporated by reference and is made a part of the subject patent application.

It is, therefore, an object of this invention to provide a method for placing embolic coils in a relatively precise manner by the use of a stabilizing delivery catheter.

Another object of the present invention is to provide a method for placing embolic coils within an aneurysm of the brain, which system is relatively simple in use for the physician.

A further object of the present invention is to provide a method for delivering medical agents such as diagnostic or therapeutic agents, and other medical agents by the use of a delivery catheter in a relatively simple, efficient and stable manner.

A still further object is to provide a delivery catheter which enables the delivery of embolic coils within an aneurysm in a relatively simple, efficient and stable manner.

Another object of the present invention is to provide a delivery catheter which may be utilized to deliver embolics, diagnostic, and therapeutic agents by way of a delivery lumen.

A further object of the present invention is to provide a delivery catheter that is relatively simple in construction.

Other objects of the present invention will become apparent from the following description.

SUMMARY OF THE INVENTION

In accordance with one aspect of the present invention, there is provided a method for placing an embolic coil into an aneurysm, such as an aneurysm within the brain, by use of a delivery catheter. The delivery catheter includes a first lumen and a second lumen with a side opening which extends positioned generally proximal to the distal end of the catheter. The delivery catheter also includes a puller wire which extends through the first lumen and is fixedly attached to the delivery catheter at a location proximal to the distal end of the catheter. The method comprises the steps of introducing the delivery catheter into the vessel of a patient over a guidewire. The guidewire extends through the second lumen and serves to generally align the side opening with the aneurysm. The method also includes the steps of withdrawing the guidewire, pulling the proximal end of the puller wire to cause the delivery catheter to deflect, or bow, at a location proximal to the side opening to thereby cause the side opening to move in a position adjacent to the aneurysm, introducing an embolic coil deployment device into the delivery catheter through the second lumen and then through the side opening into the aneurysm, delivering an embolic coil into the aneurysm, withdrawing the embolic coil deployment device from the delivery catheter, releasing the proximal end of the puller wire to permit the catheter to straighten, and thereafter withdrawing the delivery catheter from the vessel of the patient.

In accordance with another aspect of the present invention, there is provided a method for placing a medical agent, which may take the form for example of a diagnostic or therapeutic device, or a liquid embolic material, or an embolic coil, at a preselected position within a vessel of the body. The method utilizes a delivery catheter having a first and second lumen and a side opening in the second lumen proximal the distal end of the catheter. Also the catheter includes a puller wire which extends through the first lumen and is fixedly attached to the delivery catheter at a location proximal to the distal end of the catheter. The method comprises the steps of pre-loading the delivery catheter with a guidewire by placing the guidewire into the second lumen, thereafter introducing the catheter into the vessel of a patient to generally align the side opening of the catheter at a preselected position within the vessel, pulling the proximal end of the puller wire to cause the catheter to deflect, or bow, at the preselected position within the vessel to thereby stabilize the catheter within the vessel, withdrawing the guidewire, introducing a deployment device for carrying the medical agent into the second lumen of the delivery catheter and through the side opening to deliver the medical agent at the preselected position, releasing the proximal end of the puller wire to permit the delivery catheter to become straighten, and thereafter withdrawing the delivery catheter from the vessel of the patient.

In accordance with other embodiments of the present invention, the method may include delivery of a medical agent which takes the form of a diagnostic or therapeutic agent, an embolic coil, or other medicament.

In accordance with still another embodiment of the invention, the method includes the use of a hydraulic deployment system for delivering an embolic coil through a delivery catheter to an aneurysm. The hydraulic deployment device includes a positioning catheter having a distal tip for retaining the embolic coil. When the positioning catheter is pressurized with a fluid, the distal tip of the positioning catheter expands outwardly to release the coil at the preselected position within the aneurysm.

In accordance with another aspect of the present invention there is provided an apparatus for placing an embolic agent into a vessel. The apparatus comprises a delivery catheter having a proximal section, a distal section and an intermediate section which is formed of a relatively flexible polymeric material. The catheter also includes a side opening at a location within the intermediate section, and a puller wire extending through the first lumen and being fixedly attached to the delivery catheter at a location proximal the distal end of the catheter. When the puller wire is pulled proximately the relatively flexible intermediate section deflects to thereby cause the side opening of the catheter to move laterally with respect to the catheter.

A more detailed explanation of the invention is provided in the following description and claims, and is illustrated in the accompanying drawings.

BRIEF DESCRIPTION OF THE DRAWINGS

FIG. 1 is a partial sectional view of a delivery catheter constructed in accordance with the principles of the present invention;

FIG. 2 is a partial sectional view of a vascular occlusive coil deployment system that may be used with the delivery catheter of FIG. 1;

FIG. 3 is a side elevational view of the delivery catheter of FIG. 1 in use to delivery an embolic coil to an aneurysm;

FIG. 4 is a cross-sectional view of the catheter of FIG. 3, taken along the plane of the line 5–5 ' of FIG. 3;

FIG. 5 is a cross-sectional view of the catheter of FIG. 3, taken along the plane of line 5–5' of FIG. 3; and, FIGS. 6 through 8 are diagrammatic sequential views of a method of placing embolic coils in accordance with an embodiment of the present invention.

DESCRIPTION OF THE PREFERRED EMBODIMENT

Figure 6:
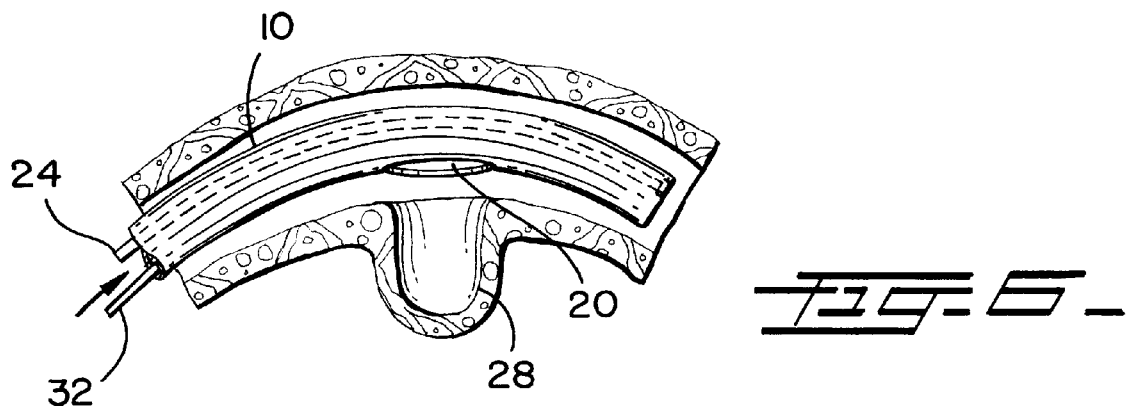

FIG. 1 generally illustrates the construction of a preferred embodiment of the delivery catheter of the present invention which generally comprises a dual lumen catheter 10 having a "Y" connector 12 coupled to the proximal end of the catheter. More particularly, the dual lumen catheter includes a first lumen 14 and a second lumen 16. The second lumen 16 extends from the proximal end of the catheter to the distal end of the catheter and also communicates with a lumen 18 which extends from the distal end to the proximal end of the "Y" connector 12. As illustrated, a side opening 20 extends from the second lumen 16 through the side wall of the catheter at a position which is slightly proximate the distal tip of the delivery catheter 10. This side opening, as will be subsequently explained in more detail, serves to permit the introduction of an embolic coil deployment device into an aneurysm for placement of an embolic coil into the aneurysm.

As further illustrated in FIG. 1, the first lumen 14 extends from the proximal end of the delivery catheter 10 to a position slightly proximal the location on the catheter of the side opening 20. At that point the first lumen 14 exits the side wall of the catheter. A corresponding first lumen 14a extends along the same axis as lumen 14, but extends from the distal end of the catheter and also exits through the side wall of the catheter at a position slightly distal on the catheter of the side opening 20. In addition, the proximal end of the first lumen 14 communicates with a second passageway in the "Y" connector 12 and extends out of the side port 22 of the "Y" connector 12. As may be seen, a puller wire 24 extends from the proximal end of the side port 22 of the "Y" connector and through the lumen 14 of the delivery catheter 10 and exits the first lumen 14 and re-enters the corresponding first lumen 14a. Still further, the puller wire 24 is fixedly attached within the corresponding first lumen 14a at the distal end of this lumen.

While the delivery catheter 10 may be constructed of various flexible materials including various polymers, preferably, the catheter 10 is formed in three different sections of materials having different durometers and different polymer compositions. The proximal section of the catheter 23A, designated as "A" is preferably formed of a nylon material having a durometer of about 75D and extends for a length of about 100 centimeters. The intermediate section 23B, designated "B", is preferably formed of a pellethane material having a durometer of about 65D and is generally about 40 centimeters in length, and the distal section 23C of the catheter, designated "C", is preferably formed of a pellethane material having a durometer of about 80A and extends for a length of about 10 centimeters. With this construction the catheter is sufficiently flexible to be delivered through the various tortuous vessels of the human brain but at the same time provides sufficient rigidity or "back-up" support for introducing the catheter into and through these vessels. This construction also makes possible the ease of deflection, or bowing, of the intermediate section 23B.

FIG. 2 illustrates a hydraulic occlusive coil deployment device 100 which is comprised of a hydraulic injector, or syringe, 102, coupled to the proximal end of a positioning catheter 104. An embolic coil 106 is disposed within the lumen at the distal section 108 of the catheter. The proximal end of the coil 106 is tightly held within the lumen of the distal section 108 of the catheter 104 until the deployment device is activated for release of the coil. As may be seen, the syringe 102 includes a threaded piston 110 which is controlled by the handle 112 for infusing fluid into the interior of the catheter 104. Also, as illustrated, the catheter 104 includes a winged hub 114 which aids in the insertion of the catheter.

The embolic coil 106 may take various forms and configurations, and may even take the form of a randomly wound coil. Preferably, the distal section of the coil deployment device 100 is formed of a polymeric material with a relatively low durometer which exhibits the characteristic that, when a fluid pressure of approximately 300 psi is applied to the interior of the catheter, the walls of the distal section 108 expand radially, somewhat similar to the action of a balloon inflating, to thereby release the proximal end of the coil 106. Reference is made to the above-mentioned U.S. Pat. No. 6,113,622 for a more detailed description of the hydraulic occlusive coil deployment device 100.

FIG. 3 illustrates in detail the delivery catheter 10 which has been inserted into a blood vessel 26 of the brain in order to place an embolic coil 106 into an aneurysm 28. FIGS. 4 and 5 illustrate cross-sections taken through the delivery catheter 10 at locations indicated by 4–4' prime and 5–5', respectively, shown in FIG. 3. More particularly, FIG. 4 in conjunction with FIG. 3 illustrates the location 30 where the puller wire 24 exits and re-enters through the side wall of the catheter. Also illustrated in FIG. 4 is an end view of the embolic coil deployment device which extends through the side opening 20 of the catheter 10. FIG. 5 illustrates a sectional view of the delivery catheter 10 with the first lumen 14 and second lumen 16 which serve to carry the puller wire 24 and the embolic coil deployment device 100.

Figure 7:
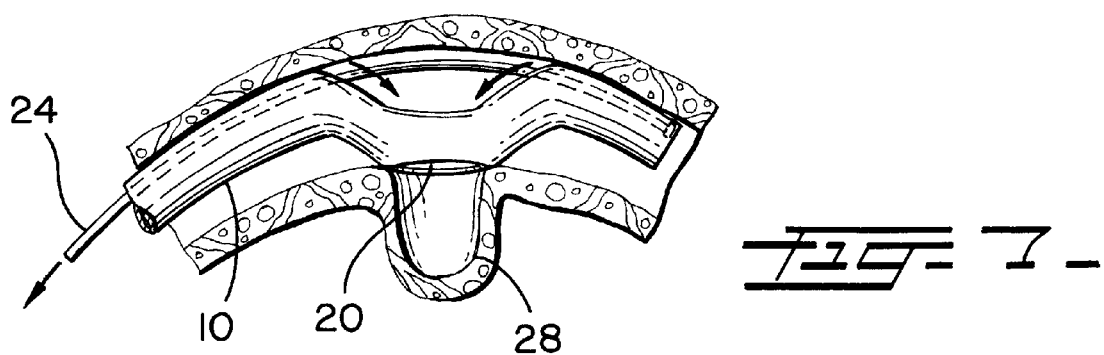
Figure 8:
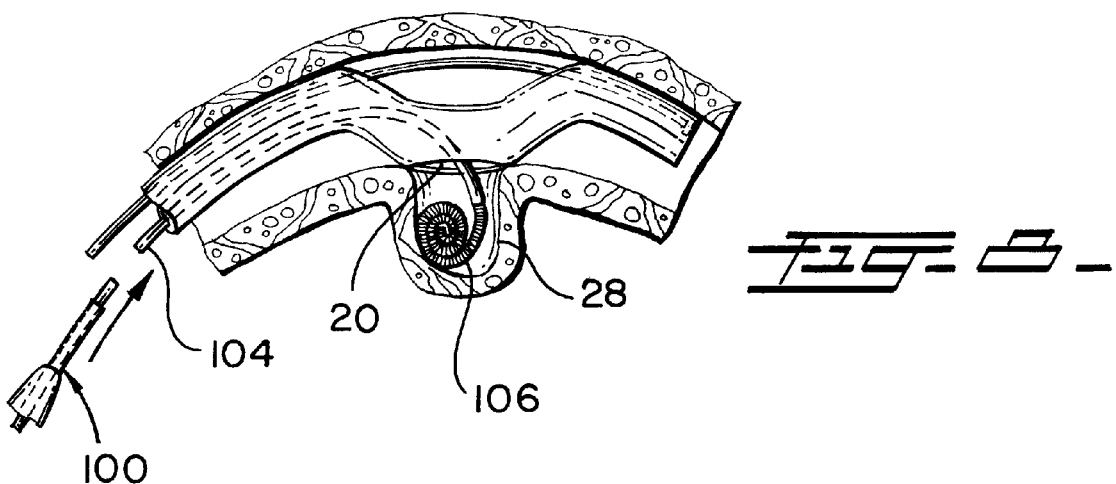

Reference is made to FIGS. 3 and 6 through 8 for an understanding of the operation of the delivery catheter used in conjunction with the embolic coil deployment device 100. As illustrated in FIG. 6, the delivery catheter is inserted into a vessel, preferably over a guidewire 32, and is positioned such that the side opening 20 is adjacent to an aneurysm 28. The guidewire 32 is then removed. Thereafter, the puller wire 24 is pulled proximally, as illustrated in FIG. 7, to thereby cause the delivery catheter 10 to deflect, or bow, in the region where the side opening 20 is located to thereby cause the side opening to essentially mate with the opening of the aneurysm 28. Once the opening has been positioned at the mouth of the aneurysm 28, the embolic coil deployment device 100 may then be inserted through the second lumen and then out of the side opening 20 and into the aneurysm 28. An embolic coil 106 may then be placed into the aneurysm and released from the distal end of the deployment device 100. The deployment device 100 may then be removed and this process may be repeated until such time as sufficient coils have been placed into the aneurysm. When the aneurysm 28 has been sufficiently filled with embolic coils, the coil deployment device may be removed from the delivery catheter. Thereafter, the puller wire may be released to thereby permit the catheter to straighten within the vessel. Once the catheter has straightened within the vessel, the catheter may be easily withdrawn from the vessel and from the body of the patient.

As may be appreciated, with the present invention it is possible to stabilize the delivery catheter at a position where the side opening of the delivery catheter is adjacent to the aneurysm. Embolic coils may be delivered through the side opening of the delivery catheter directly into the aneurysm with relatively good precision. With this system it is possible to fill an aneurysm with a plurality of embolic coils in very short order without the loss of coils into the main blood vessel, or other vessels within the body. These and other advantageous of this invention will become more apparent from an understanding of the invention as claimed.

A novel system and method have been disclosed in which an embolic coil, or coils, may be securely placed within an aneurysm with a delivery catheter which is stabilized. Although an illustrative embodiment of the invention has been shown and described, it is to be understood that various modifications and substitutions may be made by those skilled in the art without departing from the spirit and scope of the present invention. Further, in addition to the delivery of embolic coils, the system may be utilized to deliver other medical agents such as diagnostic or therapeutic agents of various types including liquid embolic materials. Other modifications may be made which would be within the spirit and the scope of the following claims.

That which is claimed is:

1. A method for placing an embolic coil into an aneurysm comprising the steps of:
   providing a delivery catheter having a proximal end and a distal end, a first lumen and a second lumen with a side opening from the second lumen proximal the distal end of the catheter, and a puller wire extending through said first lumen and being fixedly attached to the delivery catheter at a location proximal the distal end of the catheter;
   introducing the delivery catheter into the vessel of a patient over a guidewire extending through the second lumen to generally align the side opening of the delivery catheter with the aneurysm;
   withdrawing the guidewire;
   pulling the proximal end of the puller wire to cause the delivery catheter to deflect at a location proximal to the side opening in said second lumen to thereby cause the side opening to move to a position adjacent to the aneurysm;
   introducing an embolic coil deployment device into the delivery catheter through the second lumen and through the side opening;
   delivering an embolic coil into the aneurysm;
   withdrawing the embolic coil deployment device from the delivery catheter;
   releasing the proximal end of the puller wire to permit the catheter to straighten; and,
   thereafter withdrawing the delivery catheter from the vessel of the patient.

2. A method for placing a medical agent at a preselected position within a vessel comprising the steps of:
   providing a delivery catheter having a proximal end and a distal end, a first lumen and a second lumen with a side opening from the second lumen proximal to the distal end of the catheter, and a puller wire extending through said first lumen and being fixedly attached to the delivery catheter at a location proximal to the distal end of the catheter;
   preloading the delivery catheter with a guidewire extending through said second lumen;
   thereafter introducing the catheter into the vessel of a patient to generally align the side opening at a preselected position within a vessel;
   pulling the proximal end of the puller wire to cause the catheter to bow at the preselected position within the vessel to thereby stabilize the position of the catheter;
   withdrawing the guidewire;
   introducing a medical agent deployment device into the second lumen of the delivery catheter and through the side opening;
   delivering the medical agent at the preselected position;
   releasing the proximal end of the puller wire to permit the delivery catheter to straighten; and,
   thereafter withdrawing the delivery catheter from the vessel of the patient.

3. A method as defined in claim 2, wherein said medical agent comprises an embolic coil.

4. A method as defined in claim 2, wherein said medical agent comprises a therapeutic agent.

5. A method as defined in claim 2, wherein said medical agent comprises a diagnostic agent.

6. A method for placing an embolic agent into an aneurysm comprising the steps of:
   providing a delivery catheter having a proximal section, a distal section and an intermediate section which is formed of a relatively flexible polymeric material, said catheter having a first lumen and a second lumen with a side opening from the second lumen at a location within the intermediate section of the catheter, and a puller wire extending through said first lumen and being fixedly attached to the delivery catheter at a location proximal the distal end of the catheter;
   introducing the delivery catheter into the vessel of a patient over a guidewire extending through the second lumen to generally align the side opening of the delivery catheter with the aneurysm;
   withdrawing the guidewire;
   pulling the proximal end of the puller wire to cause the intermediate section of the delivery catheter to deflect at a location proximal to the side opening in said second lumen to thereby cause the side opening to move to a position adjacent to the aneurysm;
   introducing an embolic agent deployment device into the delivery catheter through the second lumen and through the side opening;
   delivering the embolic agent into the aneurysm;

withdrawing the embolic agent deployment device from the delivery catheter;

releasing the proximal end of the puller wire to permit the catheter to straighten; and, thereafter withdrawing the delivery catheter from the vessel of the patient.

7. A method as defined in claim 6 wherein said embolic agent is an embolic coil.

8. An apparatus for placing an embolic coil into an aneurysm comprising:

a delivery catheter having a proximal section, a distal section and an intermediate section which is formed of a relatively flexible polymeric material, said catheter having a first lumen and a second lumen with a side opening at a location within the intermediate section of the catheter, said second lumen being adapted to receive the embolic coil and a puller wire extending through said first lumen and being fixedly attached to the delivery catheter at a location proximal the distal end of the catheter so that when said puller wire is pulled proximately the relatively flexible intermediate section deflects to thereby cause the side opening to move laterally with respect to the catheter, so that the coil is delivered to the aneurysm through the side opening.

* * * * *